United States Patent
DiGiulio et al.

(10) Patent No.: US 10,995,045 B2
(45) Date of Patent: May 4, 2021

(54) ISOMERIZATION ZONE IN ALKYLATE COMPLEX

(71) Applicant: UOP LLC, Des Plaines, IL (US)

(72) Inventors: Christopher DiGiulio, Elmhurst, IL (US); Charles P. Luebke, Mount Prospect, IL (US); David J. Shecterle, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 50 days.

(21) Appl. No.: 16/154,985

(22) Filed: Oct. 9, 2018

(65) Prior Publication Data

US 2020/0109096 A1    Apr. 9, 2020

(51) Int. Cl.
  *C07C 5/327* (2006.01)
  *C07C 2/56* (2006.01)
  *C07C 5/27* (2006.01)

(52) U.S. Cl.
  CPC ............. *C07C 5/327* (2013.01); *C07C 2/56* (2013.01); *C07C 5/2767* (2013.01)

(58) Field of Classification Search
  CPC ........... C07C 5/27; C07C 5/2767; C07C 2/56; C07C 5/13; C07C 5/2702
  See application file for complete search history.

(56) References Cited

U.S. PATENT DOCUMENTS

| | | | |
|---|---|---|---|
| 2,330,206 A | 7/1941 | Dryer et al. | |
| 2,293,705 A | 8/1942 | Bloch | |
| 2,393,857 A | 12/1942 | Frey | |
| 2,315,197 A | 3/1943 | Goldsby et al. | |
| 2,415,733 A | 5/1943 | D'Ouville | |
| 2,456,672 A | 3/1945 | Bloch et al. | |
| 2,397,085 A | 6/1945 | Boedeker et al. | |
| 2,395,543 A | 2/1946 | Gallagher | |
| 2,404,483 A | 7/1946 | Frey | |
| 2,461,153 A | 2/1949 | Goldsby | |
| 3,050,456 A | 8/1962 | Melchior | |
| 3,223,749 A * | 12/1965 | Van Pool | C07C 2/62 585/701 |
| 4,341,911 A * | 7/1982 | Vora | C07C 9/14 585/314 |

(Continued)

FOREIGN PATENT DOCUMENTS

| | | | |
|---|---|---|---|
| FR | 840717 A | 5/1939 | |
| FR | 2775283 A1 | 8/1999 | |

(Continued)

OTHER PUBLICATIONS

Liu Nana, et al., Significance of Integration of Normal Butane Isomerization with Alkylation for Gasoline Blending, www.cnki.com.cn, Petroleum Refinery Engineering, Sep. 2013 (Abstract Only).

*Primary Examiner* — Youngsul Jeong
*Assistant Examiner* — Jason Y Chong

(57) ABSTRACT

An alkylation process including an upfront isomerization zone is described. 100% n-butane or field butanes can be converted into a blend of approximately 60 wt % isobutane and 40 wt % n-butane in the isomerization zone. This blend can be used as the feed to all types of alkylation zones. It stabilizes the feed composition so that the dehydrogenation zone and alkylation zone always operate with the same feed.

17 Claims, 4 Drawing Sheets

(56) References Cited

U.S. PATENT DOCUMENTS

| | | | |
|---|---|---|---|
| 4,367,357 A | * | 1/1983 | Vora .................. C07C 9/16 585/314 |
| 4,393,250 A | | 7/1983 | Gottlieb et al. |
| 4,868,342 A | * | 9/1989 | Verson ................ C07C 9/16 568/697 |
| 5,475,175 A | | 12/1995 | Husain et al. |
| 5,689,015 A | | 11/1997 | Hunt et al. |
| 6,768,035 B2 | | 7/2004 | O'Rear et al. |
| 6,897,345 B2 | | 5/2005 | Marchionna et al. |
| 7,439,410 B1 | | 10/2008 | Rice et al. |
| 8,728,301 B2 | | 5/2014 | Timken |
| 9,434,662 B2 | | 9/2016 | Pham et al. |
| 2010/0076096 A1 | | 3/2010 | Calis et al. |
| 2017/0342002 A1 | * | 11/2017 | Zavala ................ C10G 9/00 |

FOREIGN PATENT DOCUMENTS

| | | |
|---|---|---|
| GB | 575797 A | 3/1946 |
| RU | 2161147 | 12/2009 |

* cited by examiner

ISOMERIZATION ZONE IN ALKYLATE COMPLEX

BACKGROUND

A process for the conversion of paraffins to olefins involves passing a paraffin stream over a highly selective catalyst, where the paraffin is dehydrogenated to the corresponding olefin. The dehydrogenation reaction is achieved under operating conditions selected to minimize the loss of feedstock.

The typical process involves the use of a reactor (e.g., radial flow, fixed bed, fluidized bed, and the like) where a paraffin feedstock is contacted with a dehydrogenation catalyst under reaction conditions. The process involves dehydrogenating paraffins in the $C_2$ to $C_{17}$ range to produce olefins used as monomers used in the formation of polymers, or as plasticizers, or for dehydrogenating paraffins in the $C_{10}$ to $C_{14}$ range to produce olefins for the production of alkyl benzenes (LABs), for dehydrogenating paraffins in the $C_{12}$ to $C_{17}$ range to produce detergent alcohols or olefin sulfonates, and for producing $C_4$ olefins for the production of methyl tert-butyl ether (MTBE) or alkylate gasoline.

A $C_4$ based dehydrogenation unit can be used to produce a $C_4$ olefin containing stream which can be sent to a downstream alkylation unit. As an example, sulfuric acid alkylation prefers $C_4$ olefins as a feedstock because alkylation with n-butene and isobutane produces higher octane alkylate than alkylation with isobutylene and isobutane, as high octane alkylate is synonymous with high octane gasoline. Typically, olefins are either externally purchased or are present in internal refinery streams. Recent changes in feedstock pricing and feedstock availability have created interest in first producing the olefins using the dehydrogenation process, followed by subsequent alkylation.

SUMMARY AND DETAILED DESCRIPTION

Butenes and butadienes are important chemical precursors for rubbers, polymers, and other materials used in common products. N-butenes and isobutylene are also used in the production of alkylate, which can be used in a blending pool for gasoline.

The alkylation of $C_4$ olefins to form alkylate is performed in an alkylation process. Several types of alkylation are available, including, but not limited to, sulfuric acid (SA) alkylation, hydrofluoric acid (HF) alkylation, and ionic liquids (IL) alkylation. Depending on the method used, the preferred olefin feedstock changes. For example, the preferred olefin feedstock for HF alkylation is an isobutylene feedstock, while the preferred feed for SA alkylation is an n-butene feedstock.

Figure 1:
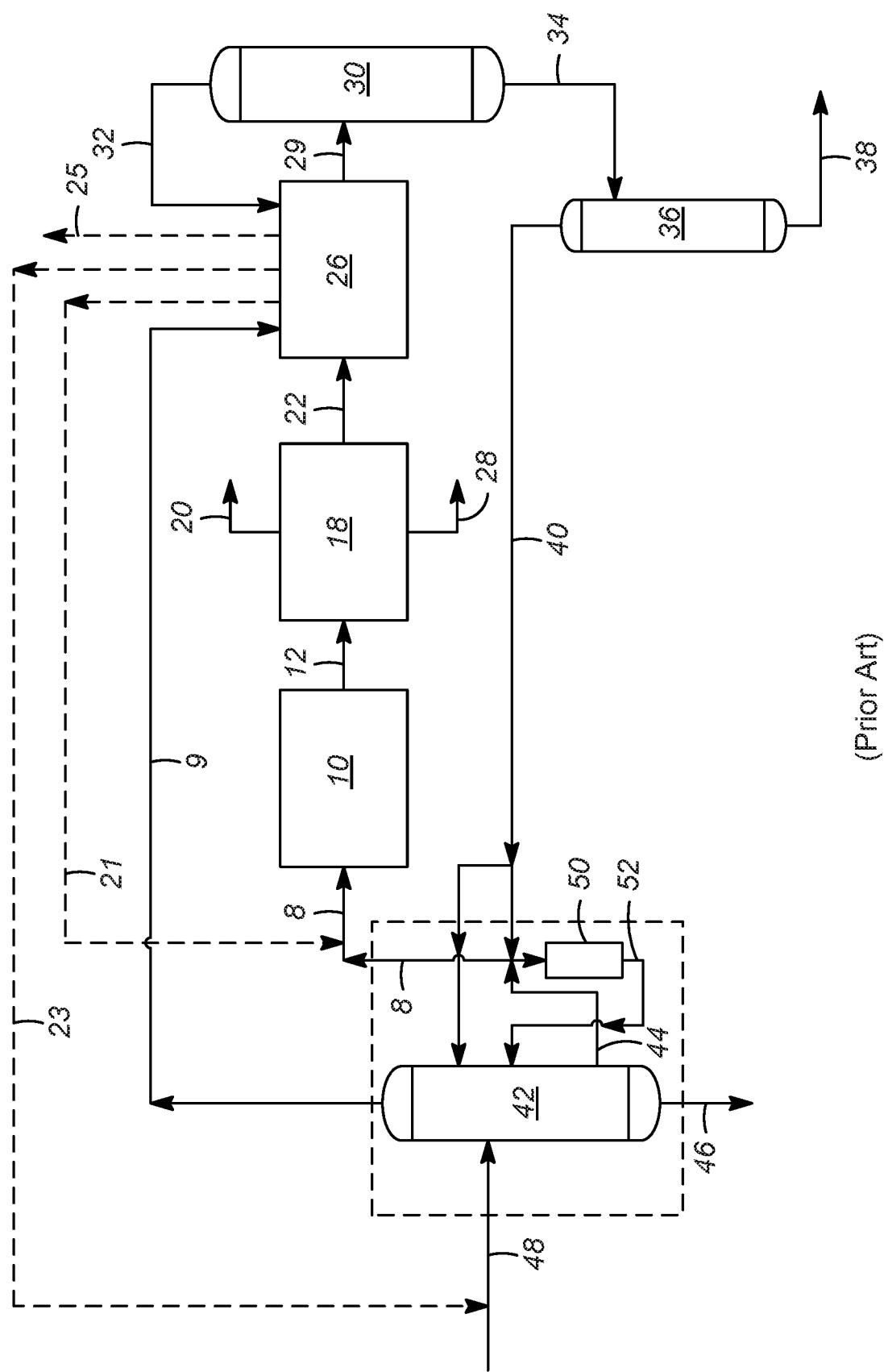
FIG. 1 illustrates one example of a prior art process.

In the process configuration shown for the prior art configuration (FIG. 1), the feedstock to the dehydrogenation zone can be selected such that preferred olefin is produced as feed to the downstream alkylation unit. The process configuration shown in FIG. 1 shows how that could be configured when the downstream alkylation unit is SA alkylation unit. This process configuration produces the maximum n-butene, which is the preferred feedstock for the SA Alkylation unit. However, it requires additional equipment (such as the feed deisobutanizer associated with the isomerization zone) and additional utilities for the complex. It does not maximize octane-barrel yield (defined as octane times barrel of alkylate produced). Also, it is not flexible with respect to fresh butane feedstock composition as the deisobutanizer associated with the isomerization zone may need to be oversized to accommodate a range of fresh butane feedstock compositions.

In a process including an upfront isomerization zone, such as a butane isomerization zone, 100% n-butane or field butanes can be converted into a blend of approximately 60 wt % isobutane and 40 wt % n-butane referred to as isomerate. This blend can be used as the feed to the dehydrogenation zone which will produce an olefin product that is suitable to all types of alkylation zones despite of the feedstock preferences described above. The upfront isomerization zone additionally stabilizes the feed composition so that the dehydrogenation zone and alkylation zone always operate with the same feed, despite any changes in feed purity to the complex. By "approximately," we mean ±20 wt % (i.e., 40-80 wt % isobutane and 20-60 wt % n-butane), ±15 wt %, ±10 wt %, ±5 wt %, or ±4 wt %, or ±3 wt %, or ±2 wt %, relative to the 60 wt % isobutane and 40 wt % n-butane described previously.

This arrangement is advantageous because it removes the need for a feed deisobutanizer column. Furthermore, because the dehydrogenation zone yields isobutane, isobutene, n-butane and n-butenes as products, and everything except n-butane reacts in the alkylation zone, the lower n-butane concentration in the feed means that less n-butane passes through the alkylation zone un-reacted, minimizing n-butane recycle and treatment. Also, because there is less n-butane in the system, there is less feed going to the alkylation zone deisobutanizer.

Placement of the isomerization zone in this location also represents the best option for integration with any type of alkylation zone because the isomerization zone is not impacted by how the streams are treated inside the alkylation facility. In addition, this option is expected to have higher $C_4$ retention to olefins in the dehydrogenation zone due to differences in the thermal cracking rates of isobutane and n-butane. Lastly, the alkylation feed pre-treatment section can be operated to provide more advantageous feedstock via a selective hydrogenation zone with or without butene-1 to butene-2 isomerization capabilities.

In some embodiments, a distillation column is added downstream of the isomerization zone to remove any trace heavies produced in the isomerization zone before it is sent to the dehydrogenation zone. It also offers the advantage that any $C_5$'s in the fresh butane feed can be sent directly to the alkylate pool. The distillation column also prevents $C_8^+$ type material from entering the dehydrogenation zone in the event of an upset in the debutanizer column inside in the alkylation zone.

On aspect of the invention is a process for dehydrogenation and alkylation. In one embodiment, the process includes passing a hydrocarbon stream comprising n-butane to an isomerization zone to generate an isomerization zone product stream comprising approximately 60 wt % isobutane and 40 wt % n-butane. The isomerization zone product stream is passed to a dehydrogenation zone to generate a dehydrogenation zone product stream comprising mixed butenes, iso-butane and n-butane, wherein the mixed butenes comprise approximately 60 wt % isobutene and 40 wt % n-butene. The dehydrogenation zone product stream is passed to an alkylation zone to produce an alkylation zone product stream. The alkylation zone product stream is passed to a separation zone to generate an isobutane stream, an n-butane stream, and an alkylate product stream. The n-butane stream is passed to the isomerization zone.

In some embodiments, the separation zone comprises a deisobutanizer and a debutanizer and wherein passing the alkylation zone product stream to the separation zone comprises: passing the alkylation zone product stream to the deisobutanizer to generate the isobutane stream and a deisobutanizer bottoms stream; and passing the deisobutanizer bottoms stream to the debutanizer to generate the n-butane stream and the alkylate product stream.

In some embodiments, the separation zone comprises a distillation column and wherein passing the alkylation zone product stream to the separation zone comprises: passing the alkylation zone product stream to the distillation column to generate the isobutane stream, the n-butane stream, and the alkylate product stream.

In some embodiments, passing the isomerization zone product stream to the dehydrogenation zone comprises: passing the isomerization zone product stream to a distillation column to generate a distillation overhead stream and a distillation bottom stream; and passing the distillation overhead stream to the dehydrogenation zone.

In some embodiments, the process further comprises passing the distillation bottom stream to the separation zone.

In some embodiments, the process further comprises passing the distillation overhead stream to the alkylation zone.

In some embodiments, the process further comprises passing the isobutane stream to the alkylation zone.

In some embodiments, the process further comprises passing a portion of the isobutane stream to the dehydrogenation zone.

In some embodiments, the process further comprises passing a portion of the isomerization zone product stream to the alkylation zone.

In some embodiments, passing the dehydrogenation zone product stream to the alkylation zone comprises: passing the dehydrogenation zone product stream to a selective hydrogenation zone to generate a selective hydrogenation zone product stream; and passing the selective hydrogenation zone product stream to the alkylation zone.

In some embodiments, the selective hydrogenation zone is operated to generate a ratio of 2-butene to 1-butene greater than 8 to 1 on a weight basis.

In some embodiments, passing the dehydrogenation zone product stream to the alkylation zone comprises: passing the dehydrogenation zone product stream to a dehydrogenation fractionation zone to generate a light stream, a heavies stream, and a dehydrogenation fractionation product stream; and passing the dehydrogenation fractionation product stream to the alkylation zone.

In some embodiments, the alkylation zone is a sulfuric acid alkylation zone, or a hydrofluoric acid alkylation zone, or an ionic liquid alkylation zone.

In some embodiments, the process further comprises passing a portion of the n-butane stream to a second isomerization zone to generate a second isomerization zone product stream; and passing the second isomerization zone product stream to the separation zone.

In some embodiments, the process further comprises passing a separation zone side cut stream to a third isomerization zone to generate a third isomerization zone product stream; and passing the third isomerization zone product stream to the separation zone.

In some embodiments, the process further comprises at least one of: sensing at least one parameter of the process and generating a signal or data from the sensing; generating and transmitting a signal; or generating and transmitting data.

In some embodiments, the hydrocarbon stream comprises at least 50% n-butane by weight, or at least 60% n-butane by weight, or at least 70% n-butane by weight, or at least 80% n-butane by weight, or at least 90% n-butane by weight.

Another aspect of the invention is a process for dehydrogenation and alkylation. In one embodiments, the process comprises passing a hydrocarbon stream comprising n-butane to an isomerization zone to generate an isomerization zone product stream comprising approximately 60 wt % isobutane and 40 wt % n-butane. The isomerization zone product stream is passed to a dehydrogenation zone to generate a dehydrogenation zone product stream comprising mixed butenes, iso-butane, and n-butane, wherein the mixed butenes comprise approximately 60 wt % isobutene and 40 wt % n-butene. The dehydrogenation zone product stream is passed to an alkylation zone to produce an alkylation zone product stream. The alkylation zone product stream is passed to a deisobutanizer to generate an isobutane stream and a deisobutanizer bottoms stream. The deisobutanizer bottoms stream is passed to a debutanizer to generate an n-butane stream and a alkylate product stream.

In some embodiments, passing the dehydrogenation zone product stream to the alkylation zone comprises: passing the dehydrogenation zone product stream to a selective hydrogenation zone to generate a selective hydrogenation zone product stream; passing the selective hydrogenation zone product stream to a dehydrogenation fractionation zone to generate a dehydrogenation fractionation product stream; and passing the dehydrogenation fractionation product stream to the alkylation zone.

In some embodiments, passing the isomerization zone product stream to the dehydrogenation zone comprises: passing the isomerization zone product stream to a distillation column to generate a distillation overhead stream and a distillation bottom stream; and passing the distillation overhead stream to the dehydrogenation zone.

By "passing a stream" to a zone, we mean passing at least a portion of the stream to the zone, up to and including the whole stream (e.g., greater than 10%, greater than 20%, greater than 30%, greater than 40%, or greater than 50%, or greater than 60%, or greater than 70%, or greater than 80%, or greater than 90%). The stream can be sent directly to the zone, or it can be sent through other zones before being sent to the specified zone. By "passing a portion of stream" to a zone, we mean passing less than the whole stream to the zone (e.g., less than 90%, less than 80%, less than 70%, less than 60%, or less than 50%, or less than 40%, or less than 30%, or less than 20%, or less than 10%).

FIG. 1 illustrates one example of a prior art process configuration to maximize the production of n-butene for a sulfuric acid type alkylation zone. This configuration consists of passing a hydrocarbon stream 8 to a dehydrogenation zone 10 to generate a first process stream 12 comprising olefins. The dehydrogenation zone 10 additionally produces a product stream comprising $H_2$ (not shown). The first process stream 12 is passed to a dehydrogenation fractionation zone 18 (if required). The dehydrogenation fractionation zone 18 produces an overhead stream 20, a bottoms stream 28, and a product stream 22. The product stream 22 is passed to an alkylation zone 26 which produces an alkylate product stream 29, comprising alkylate and unreacted $C_4$ paraffin compounds, which is passed to a first deisobutanizer 30. In some embodiments, the dehydrogenation fractionation zone 18 may not be needed.

The deisobutanizer 30 produces an overhead isobutane containing stream 32, which is sent back to the alkylation zone 26, and a deisobutanizer bottoms stream 34, which is passed to a debutanizer 36. The debutanizer 36 produces a bottoms stream 38 comprising alkylate and an overhead stream 40 which is passed either to a second deisobutanizer 42 or to an isomerization zone 50. The second deisobutanizer 42 also receives butanes in stream 48 and produces an isobutane containing overhead stream 9 which is passed to the alkylation zone 26, a bottoms stream 46 comprising $C_{5+}$ and a side cut stream 44, of which a part can be sent to a isomerization zone 50. The amount of stream 44 sent to the isomerization zone 50 depends on the amount of stream 40 sent directly to the isomerization zone 50. The remaining flow of stream 44 becomes the n-butane containing stream 8 which enters the dehydrogenation zone 10. The isomerization zone 50 produces stream 52 which is sent back to the second deisobutanizer 42.

In an exemplary embodiment, the alkylation zone 26 may comprise a depropanizer (not shown) and a $C_{3-}$ stream, comprising predominantly $C_3$ hydrocarbons, may be withdrawn in line 21 and passed back to the butanes feed 8 and subsequently passed to the dehydrogenation zone 10. Also, optionally, a $C_3-$ purge stream may be taken out in line 25.

In alternative exemplary embodiment, the alkylation zone 26 may not comprise a depropanizer, and a $C_{4-}$ stream, comprising predominantly $C_3$ and $C_4$ hydrocarbons, may be withdrawn in line 21 and passed back to the butanes feed 8 and subsequently passed to the dehydrogenation zone 10. Also, optionally, a $C_{4-}$ purge stream may be taken out in line 25. Also, optionally, a $C_{4-}$ stream 23 may be recycled back to the second deisobutanizer 42.

Figure 2:
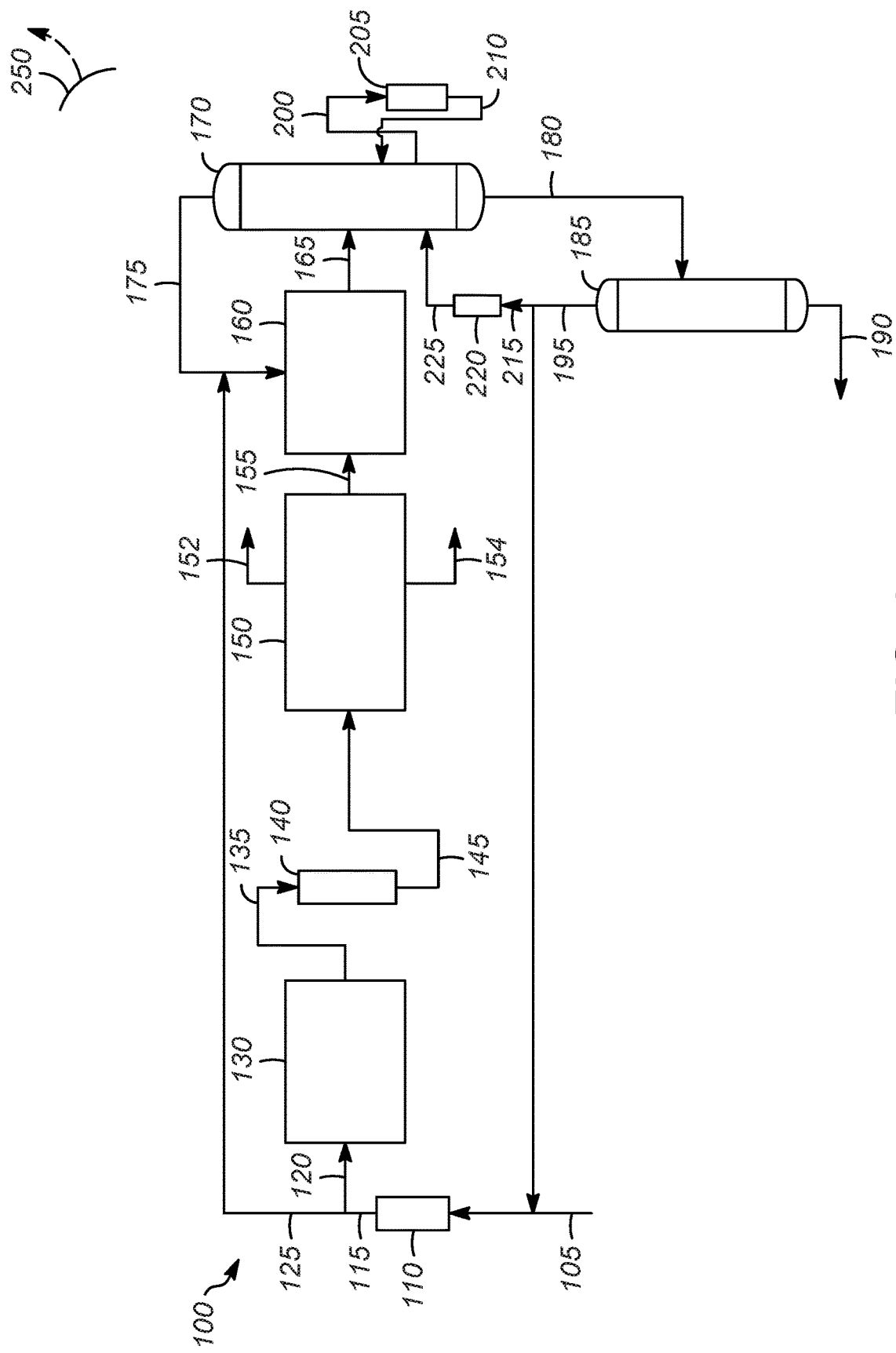
FIG. 2 illustrates one embodiment of the process of the present invention.
Figure 3:
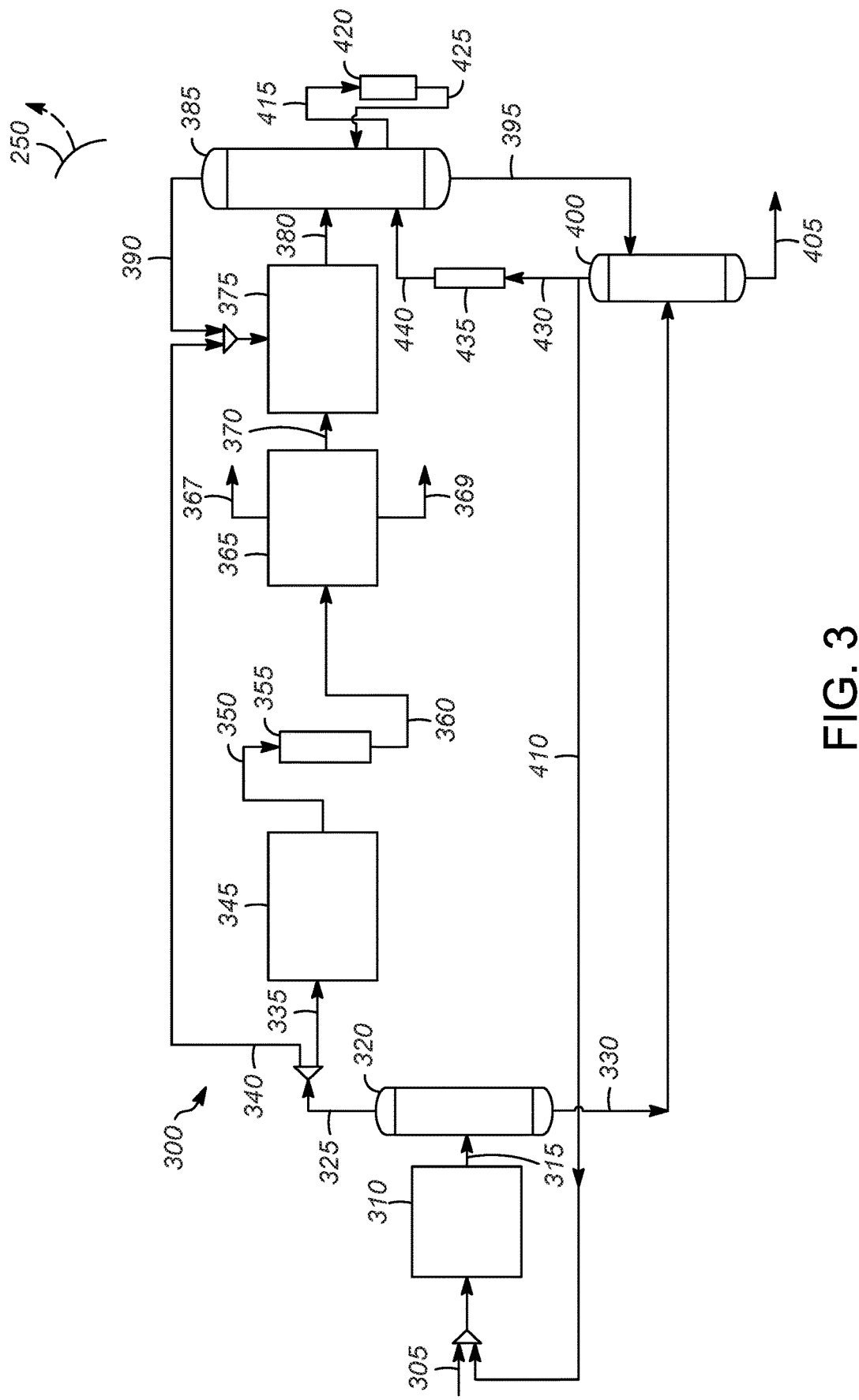
FIG. 3 illustrates another embodiment of the process of the present invention.
Figure 4:
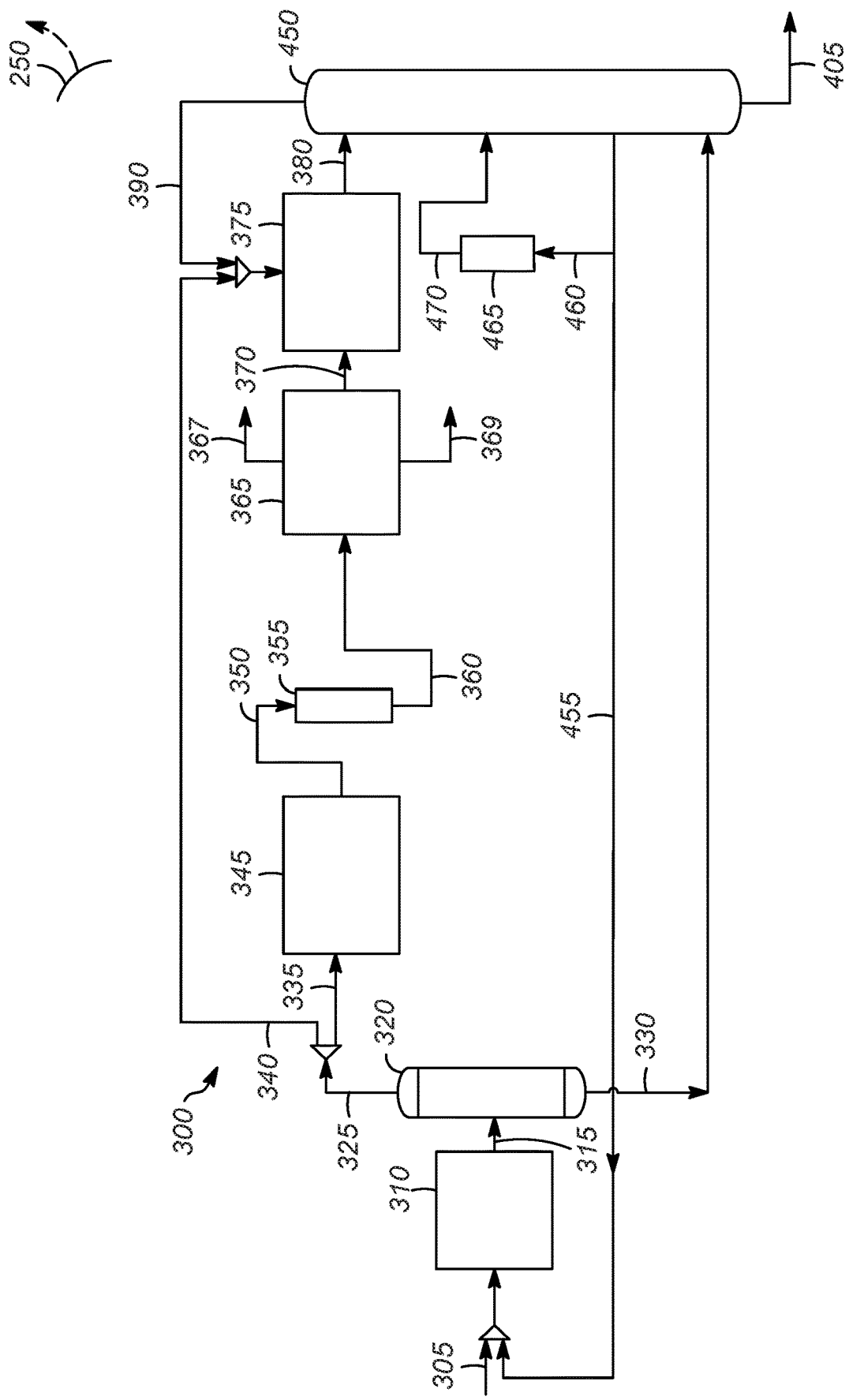
FIG. 4 illustrates another embodiment of the process of the present invention.

In the embodiments illustrated in FIGS. 2-4, there is no need for two separate deisobutanizers.

In the process 100 illustrated in FIG. 2, the butanes feed stream 105 comprises n-butane. The butanes feed stream 105 is fed into an isomerization zone 110 where the butanes are isomerized into an isomerization effluent 115 comprising a mixture of approximately 60 wt % isobutane and 40 wt % n-butane.

Isomerization effluent 115 is split into a main isomerization stream 120 and a small bypass isomerization stream 125 (if required). The main isomerization stream 120 is passed to the dehydrogenation zone 130. The dehydrogenation zone 130 produces a product stream comprising $H_2$ (not shown). The dehydrogenation zone 130 produces a dehydrogenation product stream 135 which is sent to a selective hydrogenation zone 140 to produce a selective hydrogenation product stream 145 which is sent to a dehydrogenation fractionation zone 150. In some embodiments, the selective hydrogenation zone 140 and the dehydrogenation fractionation zone 150 may not be needed.

The dehydrogenation fractionation zone 150 produces an overhead stream 152, a bottoms stream 154, and a product stream 155 which is passed to the alkylation zone 160, along with the bypass isomerization stream 125.

The alkylation zone 160 produces an alkylation product stream 165, comprising alkylate and unreacted $C_4$ compounds, which is passed to the deisobutanizer 170.

The deisobutanizer 170 produces an overhead isobutane containing stream 175, which is sent back to the alkylation zone 160, and a deisobutanizer bottoms stream 180. In some embodiments, a portion of the overhead steam 175 could be recycled back to be combined with the main isomerization stream 120 (not shown).

The deisobutanizer bottoms stream 180 is passed to the debutanizer 185 which produces a bottoms stream 190 comprising alkylate and an overhead stream 195 which is sent back to be combined with the butanes feed stream 105.

In some embodiments, a side cut 200 from the deisobutanizer 170 is sent to a second isomerization zone 205 which produces a product stream 210 which is sent back to the deisobutanizer 170. In some embodiments, a portion 215 of the overhead stream 195 from the debutanizer 185 is sent to a third isomerization zone 220 which produces stream 225 which is sent back to the deisobutanizer 170. In some embodiments, both the second isomerization zone 205 and the third isomerization zone 220 are present.

In an exemplary embodiment, the alkylation zone 160 may comprise a depropanizer (not shown) and a $C_{3-}$ stream, comprising predominantly $C_3$ hydrocarbons, may be withdrawn and passed back to the butanes feed stream 105 (not shown). Also, optionally, a $C_{3-}$ purge stream may be taken out (not shown).

In alternative exemplary embodiment, the alkylation zone 160 may not comprise a depropanizer, and a $C_{4-}$ stream, comprising predominantly $C_3$ and $C_4$ hydrocarbons, may be withdrawn and passed back to the main isomerization stream 120 (not shown). Also, optionally, a $C_{4-}$ purge stream may be taken out (not shown).

In an embodiment, the isomerization zones 110, 205, 220 may include one or more reactors, driers, a stripper column, a make-up gas compressor, and the like, as is known in the art.

In an embodiment, the selective hydrogenation zone 140 may include one or more hydrogenation reactors, a stripper column, and/or a make-up gas compressor (not shown), as is known in the art.

In an embodiment, the dehydrogenation zone 130 may include one or more dehydrogenation reactors, fired heaters, heat exchangers, quench tower, compressors, cryogenic separation system, treatment systems, fuel gas preparation system, light ends recovery, adsorption systems, fractionation columns (not shown), catalyst handling/regeneration equipment, as is known in the art.

In an embodiment, the alkylation zone 160 may include one or more alkylation reactors, heat exchangers, compressors, separation system, treatment systems, light ends recovery, fractionation columns (not shown), as is known in the art.

Any of the above lines, conduits, zones, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect. The figure shows the above categorically as 250.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein. The figure shows the above categorically as 250.

In the process 300 shown in FIG. 3, the butanes feed stream 305 comprising n-butane is fed into an isomerization zone 310 where the butanes are isomerized into an isomerization effluent 315 comprising a mixture of approximately 60 wt % isobutane and 40 wt % n-butane.

Isomerization effluent 315 is sent to a distillation column 320 where it is separated into a distillation overhead stream 325 comprising $C_{4-}$ hydrocarbons and a distillation bottoms stream 330 comprising $C_{5+}$ hydrocarbons.

The distillation overhead stream 325 is split into a main stream 335 and a make-up (if required) isobutane stream 340. The main stream 335 is passed to the dehydrogenation zone 345. The dehydrogenation zone 345 produces a dehydrogenation product stream 350 which is sent to a selective hydrogenation zone 355 to produce a selective hydrogenation product stream 360 which is sent to a dehydrogenation fractionation zone 365. In some embodiments, the selective hydrogenation zone 355 and the dehydrogenation fractionation zone 365 may not be needed.

The dehydrogenation fractionation zone 365 produces an overhead stream 367, a bottoms stream 369, and a product stream 370 which is passed to the alkylation zone 375, along with the make-up isobutane stream 340.

The alkylation zone 375 produces an alkylation product stream 380, comprising alkylate and unreacted $C_4$ compounds, which is passed to the deisobutanizer 385.

The deisobutanizer 385 produces an overhead isobutane containing steam 390, which is sent back to the alkylation zone 375, and a deisobutanizer bottoms stream 395. In some embodiments, a portion of the overhead stream 390 could be recycled back to be combined with the main stream 335 (not shown).

The deisobutanizer bottoms stream 395 and distillation bottoms stream 330 are passed to the debutanizer 400 which produces a bottoms stream 405 comprising alkylate and an overhead stream 410 comprising n-butane which is sent back to be combined with the butanes feed stream 305.

In some embodiments, a side cut 415 from the deisobutanizer 385 is sent to a second isomerization zone 420 which produces a product stream 425 which is sent back to the deisobutanizer 385. In some embodiments, a portion 430 of the overhead stream 410 from the debutanizer 400 is sent to a third isomerization zone 435 which produces stream 440 which is sent back to the deisobutanizer 385. In some embodiments, both the second isomerization zone 420 and the third isomerization zone 435 are present.

As discussed above, in an exemplary embodiment, the alkylation zone 375 may comprise a depropanizer (not shown) and a $C_{3-}$ stream, comprising predominantly $C_3$ hydrocarbons, may be withdrawn and passed back to the butanes feed stream 335 (not shown). Also, optionally, a $C_{3-}$ purge stream may be taken out (not shown).

In alternative exemplary embodiment, the alkylation zone 375 may not comprise a depropanizer, and a $C_{4-}$ stream, comprising predominantly $C_3$ and $C_4$ hydrocarbons, may be withdrawn and passed back to the main stream 335 (not shown). Also, optionally, a $C_{4-}$ purge stream may be taken out (not shown).

The isomerization zones 310, 420, 435, selective hydrogenation zone 355, dehydrogenation zone 345, and alkylation zone 375 can include the equipment described above as is known in the art.

The process 300 may include the monitoring components, etc. as described above as 250.

The processes shown in either FIG. 2 or FIG. 3 could include a combined deisobutanizer/debutanizer column rather than separate columns, as shown in FIG. 4 (where like reference numbers refer to like components and streams).

In this arrangement, the alkylation product stream 380 is sent to a combined column 450. The combined column 450 produces an overhead isobutane containing stream 390, and a bottoms stream 405 comprising alkylate.

A side cut 455 comprising n-butane is sent back to be combined with butanes feed stream 305. In some embodiments, a portion 460 of the side cut stream 455 is sent to a second isomerization zone 465 which produces a product stream 470 which is sent back to the column 450.

EXAMPLE

A case study was rigorously simulated using commercially available process simulator (such as Aspen or Unisim) to demonstrate the differences between conventional flow scheme and the current invention. The simulations allowed for relative comparisons for each section of the complex and for a complex material balance. The basis for the simulation employed the exact same amount of butane feed. For the purposes of this study, $C_{5+}$ material was excluded so that the net octane barrels shown were exclusively produced using the butane feed. Finally, sulfuric acid alkylation was assumed in this analysis. The results of the simulation are shown in Table 1.

TABLE 1

| | DEHYDRO FEED | | | FEED TO | FEED TO | FEED TO | OCTANE |
|---|---|---|---|---|---|---|---|
| | nC4 wt % | iC4 wt % | FEED DIB | DE-HYDRO | ALKY RXS | ALKY DIB | BBL PROD |
| FIG. 1 | 100 | 0 | 100% | 100% | 100% | 100% | 100.0% |
| FIG. 2 & 3 | 40 | 60 | 0% | ~100 | 85% | 66% | 100.4% |

Header: FLOWRATES RELATIVE TO FIG. 1

The results of Table 1 have been normalized such that all comparisons are made on a relative mole basis to the prior art. The feed deisobutanizer (DIB) column has been completely removed. The dehydrogenation section is approximately the same size as in the conventional flow scheme because approximately the same amount of olefins are produced. The feed to the alkylation reactors and the alkylation DIB are substantially smaller than with the conventional flow scheme because less n-butane is contained in the feed to those sections. One surprising result is that the overall octane barrel yield is higher for the flow scheme of the invention because of improved selectivity in the dehydrogenation section, even though the research octane number (RON) is expected to be slightly lower. Since the alkylation zone is processing less feed overall, the alkylation zone of the complex is expected to have a lower capital cost and to be less expensive to operate. Thus, the invention produces more octane barrels with less capital investment and lower operating costs.

While the invention has been described with what are presently considered the preferred embodiments, it is to be understood that the invention is not limited to the disclosed embodiments, but it is intended to cover various modifications and equivalent arrangements included within the scope of the appended claims.

Specific Embodiments

While the following is described in conjunction with specific embodiments, it will be understood that this description is intended to illustrate and not limit the scope of the preceding description and the appended claims.

A first embodiment of the invention is a process for dehydrogenation and alkylation, comprising passing a hydrocarbon stream comprising n-butane to an isomerization zone to generate an isomerization zone product stream comprising approximately 60 wt % isobutane and 40 wt % n-butane; passing the isomerization zone product stream to a dehydrogenation zone to generate a dehydrogenation zone product stream comprising mixed butenes, iso-butane and n-butane, wherein the mixed butenes comprise approximately 60 wt % isobutene and 40 wt % n-butene; passing the dehydrogenation zone product stream to an alkylation zone to produce an alkylation zone product stream; passing the alkylation zone product stream to a separation zone to generate an isobutane stream, an n-butane stream, and an alkylate product stream; and passing the n-butane stream to the isomerization zone. An embodiment of the invention is one, any or all of prior embodiments in this paragraph up through the first embodiment in this paragraph wherein the separation zone comprises a deisobutanizer and a debutanizer and wherein passing the alkylation zone product stream to the separation zone comprises passing the alkylation zone product stream to the deisobutanizer to generate the isobutane stream and a deisobutanizer bottoms stream; and passing the deisobutanizer bottoms stream to the debutanizer to generate the n-butane stream and the alkylate product stream. An embodiment of the invention is one, any or all of prior embodiments in this paragraph up through the first embodiment in this paragraph wherein the separation zone comprises a distillation column and wherein passing the alkylation zone product stream to the separation zone comprises passing the alkylation zone product stream to the distillation column to generate the isobutane stream, the n-butane stream, and the alkylate product stream. An embodiment of the invention is one, any or all of prior embodiments in this paragraph up through the first embodiment in this paragraph wherein passing the isomerization zone product stream to the dehydrogenation zone comprises passing the isomerization zone product stream to a distillation column to generate a distillation overhead stream and a distillation bottom stream; and passing the distillation overhead stream to the dehydrogenation zone. An embodiment of the invention is one, any or all of prior embodiments in this paragraph up through the first embodiment in this paragraph further comprising passing the distillation bottom stream to the separation zone. An embodiment of the invention is one, any or all of prior embodiments in this paragraph up through the first embodiment in this paragraph further comprising passing the distillation overhead stream to the alkylation zone. An embodiment of the invention is one, any or all of prior embodiments in this paragraph up through the first embodiment in this paragraph further comprising passing the isobutane stream to the alkylation zone. An embodiment of the invention is one, any or all of prior embodiments in this paragraph up through the first embodiment in this paragraph further comprising passing a portion of the isobutane stream to the dehydrogenation zone. An embodiment of the invention is one, any or all of prior embodiments in this paragraph up through the first embodiment in this paragraph further comprising passing a portion of the isomerization zone product stream to the alkylation zone. An embodiment of the invention is one, any or all of prior embodiments in this paragraph up through the first embodiment in this paragraph wherein passing the dehydrogenation zone product stream to the alkylation zone comprises passing the dehydrogenation zone product stream to a selective hydrogenation zone to generate a selective hydrogenation zone product stream; and passing the selective hydrogenation zone product stream to the alkylation zone. An embodiment of the invention is one, any or all of prior embodiments in this paragraph up through the first embodiment in this paragraph wherein the selective hydrogenation zone is operated to generate a ratio of 2-butene to 1-butene greater than 8 to 1 on a weight basis. An embodiment of the invention is one, any or all of prior embodiments in this paragraph up through the first embodiment in this paragraph wherein passing the dehydrogenation zone product stream to the alkylation zone comprises passing the dehydrogenation zone product stream to a dehydrogenation fractionation zone to generate a light stream, a heavies stream, and a dehydrogenation fractionation product stream; and passing the dehydrogenation fractionation product stream to the alkylation zone. An embodiment of the invention is one, any or all of prior embodiments in this paragraph up through the first embodiment in this paragraph, wherein the alkylation zone is a sulfuric acid alkylation zone, or a hydrofluoric acid alkylation zone, or an ionic liquid alkylation zone. An embodiment of the invention is one, any or all of prior embodiments in this paragraph up through the first embodiment in this paragraph, further comprising passing a portion of the n-butane stream to a second isomerization zone to generate a second isomerization zone product stream; and passing the second isomerization zone product stream to the separation zone. An embodiment of the invention is one, any or all of prior embodiments in this paragraph up through the first embodiment in this paragraph, further comprising passing a separation zone side cut stream to a third isomerization zone to generate a third isomerization zone product stream; and passing the third isomerization zone product stream to the separation zone. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data. An embodiment of the invention is one, any or all of prior embodiments in this paragraph up through the first embodiment in this paragraph wherein the hydrocarbon stream comprises at least 50% n-butane by weight.

A second embodiment of the invention is a process for dehydrogenation and alkylation, comprising passing a hydrocarbon stream comprising n-butane to an isomerization zone to generate an isomerization zone product stream comprising approximately 60 wt % isobutane and 40 wt % n-butane; passing the isomerization zone product stream to a dehydrogenation zone to generate a dehydrogenation zone product stream comprising mixed butenes, iso-butane, and n-butane, wherein the mixed butenes comprise approximately 60 wt % isobutene and 40 wt % n-butene; passing the dehydrogenation zone product stream to an alkylation zone to produce an alkylation zone product stream; passing the alkylation zone product stream to a deisobutanizer to generate an isobutane stream and a deisobutanizer bottoms stream; and passing the deisobutanizer bottoms stream to a debutanizer to generate an n-butane stream and a alkylate product stream. An embodiment of the invention is one, any or all of prior embodiments in this paragraph up through the second embodiment in this paragraph wherein passing the dehydrogenation zone product stream to the alkylation zone comprises passing the dehydrogenation zone product stream to a selective hydrogenation zone to generate a selective hydrogenation zone product stream; passing the selective hydrogenation zone product stream to a dehydrogenation fractionation zone to generate a dehydrogenation fractionation product stream; and passing the dehydrogenation fractionation product stream to the alkylation zone. An embodiment of the invention is one, any or all of prior embodiments in this paragraph up through the second embodiment in this paragraph wherein passing the isomerization zone product stream to the dehydrogenation zone comprises passing the isomerization zone product stream to a distillation column to generate a distillation overhead stream and a distillation bottom stream; and passing the distillation overhead stream to the dehydrogenation zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for dehydrogenation and alkylation, comprising:
    passing a hydrocarbon feed stream comprising n-butane to an isomerization zone to generate an isomerization zone product stream comprising approximately 60 wt % isobutane and 40 wt % n-butane;
    passing the isomerization zone product stream to a distillation column to generate a distillation overhead stream comprising C4− hydrocarbons and a distillation bottom stream comprising C5+ hydrocarbons;
    passing a first portion of the distillation overhead stream to a dehydrogenation zone to generate a dehydrogenation zone product stream comprising mixed butenes, iso-butane and n-butane, wherein the mixed butenes comprise approximately 60 wt % isobutene and 40 wt % n-butene;
    passing the dehydrogenation zone product stream and a second portion of the distillation overhead stream to an alkylation zone to produce an alkylation zone product stream;
    passing the alkylation zone product stream to a separation zone to generate an isobutane stream, an n-butane stream, and an alkylate product stream; and
    passing the n-butane stream to the isomerization zone.

2. The process of claim 1 wherein the separation zone comprises a deisobutanizer and a debutanizer and wherein passing the alkylation zone product stream to the separation zone comprises:
    passing the alkylation zone product stream to the deisobutanizer to generate the isobutane stream and a deisobutanizer bottoms stream; and
    passing the deisobutanizer bottoms stream to the debutanizer to generate the n-butane stream and the alkylate product stream.

3. The process of claim 1 wherein the separation zone comprises a distillation column and wherein passing the alkylation zone product stream to the separation zone comprises:
    passing the alkylation zone product stream to the distillation column to generate the isobutane stream, the n-butane stream, and the alkylate product stream.

4. The process of claim 1 further comprising:
    passing the distillation bottom stream to the separation zone.

5. The process of claim 1 further comprising:
    passing the isobutane stream to the alkylation zone.

6. The process of claim 1 further comprising:
    passing a portion of the isobutane stream to the dehydrogenation zone.

7. The process of claim 1 further comprising:
    passing a portion of the isomerization zone product stream to the alkylation zone.

8. The process of claim 1 wherein passing the dehydrogenation zone product stream to the alkylation zone comprises:
    passing the dehydrogenation zone product stream to a selective hydrogenation zone to generate a selective hydrogenation zone product stream; and
    passing the selective hydrogenation zone product stream to the alkylation zone.

9. The process of claim 8 wherein the selective hydrogenation zone is operated to generate a ratio of 2-butene to 1-butene greater than 8 to 1 on a weight basis.

10. The process of claim 1 wherein passing the dehydrogenation zone product stream to the alkylation zone comprises:
    passing the dehydrogenation zone product stream to a dehydrogenation fractionation zone to generate a light stream, a heavies stream, and a dehydrogenation fractionation product stream; and
    passing the dehydrogenation fractionation product stream to the alkylation zone.

11. The process of claim 1, wherein the alkylation zone is a sulfuric acid alkylation zone, a hydrofluoric acid alkylation zone, or an ionic liquid alkylation zone.

12. The process of claim 1, further comprising:
    passing a portion of the n-butane stream to a second isomerization zone to generate a second isomerization zone product stream; and
    passing the second isomerization zone product stream to the separation zone.

13. The process of claim 1, further comprising:
    passing a separation zone side cut stream comprising n-butane to a third isomerization zone to generate a third isomerization zone product stream; and
    passing the third isomerization zone product stream to the separation zone.

14. The process of claim 1, further comprising at least one of:
- sensing at least one parameter of the process and generating a signal or data from the sensing;
- generating and transmitting a signal; or
- generating and transmitting data.

15. The process of claim 1 wherein the hydrocarbon feed stream comprises at least 50% n-butane by weight.

16. A process for dehydrogenation and alkylation, comprising:
- passing a hydrocarbon feed stream comprising n-butane to an isomerization zone to generate an isomerization zone product stream comprising approximately 60 wt % isobutane and 40 wt % n-butane;
- passing the isomerization zone product stream to a distillation column to generate a distillation overhead stream comprising C4− hydrocarbons and a distillation bottom stream comprising C5+ hydrocarbons;
- passing a first portion of the distillation overhead stream to a dehydrogenation zone to generate a dehydrogenation zone product stream comprising mixed butenes, iso-butane, and n-butane, wherein the mixed butenes comprise approximately 60 wt % isobutene and 40 wt % n-butene;
- passing the dehydrogenation zone product stream and a second portion of the distillation overhead stream to an alkylation zone to produce an alkylation zone product stream;
- passing the alkylation zone product stream to a deisobutanizer to generate an isobutane stream and a deisobutanizer bottoms stream; and
- passing the deisobutanizer bottoms stream to a debutanizer to generate an n-butane stream and an alkylate product stream.

17. The process of claim 16 wherein passing the dehydrogenation zone product stream to the alkylation zone comprises:
- passing the dehydrogenation zone product stream to a selective hydrogenation zone to generate a selective hydrogenation zone product stream;
- passing the selective hydrogenation zone product stream to a dehydrogenation fractionation zone to generate a dehydrogenation fractionation product stream; and
- passing the dehydrogenation fractionation product stream to the alkylation zone.

* * * * *